(12) United States Patent
Bristow

(10) Patent No.: US 9,469,591 B2
(45) Date of Patent: Oct. 18, 2016

(54) INTEGRATED PROCESS FOR THE PRODUCTION OF METHANOL AND METHYL ACETATE

(71) Applicant: BP CHEMICALS LIMITED, Middlesex (GB)

(72) Inventor: Timothy Crispin Bristow, East Yorkshire (GB)

(73) Assignee: BP CHEMICALS LIMITED, Middlesex (GB)

(*) Notice: Subject to any disclaimer, the term of this patent is extended or adjusted under 35 U.S.C. 154(b) by 0 days.

(21) Appl. No.: 14/652,828

(22) PCT Filed: Dec. 19, 2013

(86) PCT No.: PCT/EP2013/077477
§ 371 (c)(1),
(2) Date: Jun. 17, 2015

(87) PCT Pub. No.: WO2014/096249
PCT Pub. Date: Jun. 26, 2014

(65) Prior Publication Data
US 2015/0329466 A1    Nov. 19, 2015

(30) Foreign Application Priority Data

Dec. 21, 2012 (EP) .................................... 12199082

(51) Int. Cl.
*C07C 67/37* (2006.01)
*C07C 51/09* (2006.01)
*C07C 29/151* (2006.01)

(52) U.S. Cl.
CPC ........... *C07C 51/09* (2013.01); *C07C 29/1516* (2013.01); *C07C 29/1518* (2013.01); *C07C 67/37* (2013.01); *Y02P 20/125* (2015.11)

(58) Field of Classification Search
CPC ...... C07C 67/37; C07C 29/151; C07C 41/16
See application file for complete search history.

(56) References Cited

U.S. PATENT DOCUMENTS

| | | |
|---|---|---|
| 5,502,243 A | 3/1996 | Waller et al. |
| 2006/0252959 A1 | 11/2006 | Cheung et al. |
| 2010/0121098 A1* | 5/2010 | Ditzel ..................... B01J 29/20 560/232 |

FOREIGN PATENT DOCUMENTS

| | | |
|---|---|---|
| EP | 0 529 868 A2 | 3/1993 |
| EP | 0 566 370 A2 | 10/1993 |
| EP | 0566370 A2 * | 10/1993 |
| EP | 0 801 050 A1 | 10/1997 |
| GB | 1 306 863 | 2/1973 |
| GB | 1306863 * | 2/1973 |
| WO | WO 03/097523 A2 | 11/2003 |

* cited by examiner

*Primary Examiner* — Paul A Zucker
(74) *Attorney, Agent, or Firm* — Nixon & Vanderhye P.C.

(57) ABSTRACT

Integrated process for the production of methyl acetate and methanol. The process is carried out by carbonylating dimethyl ether with synthesis gas, recovering methyl acetate and unreacted synthesis gas and supplying unreacted synthesis gas and fresh synthesis gas for methanol synthesis.

25 Claims, 3 Drawing Sheets

INTEGRATED PROCESS FOR THE PRODUCTION OF METHANOL AND METHYL ACETATE

This application is the U.S. national phase of International Application No. PCT/EP2013/077477 filed Dec. 19, 2013 which designated the U.S. and claims priority to European Patent Application No. 12199082.4 filed Dec. 21, 2012, the entire contents of each of which are hereby incorporated by reference.

The present invention relates to an integrated process for the production of methyl acetate and methanol from synthesis gas and dimethyl ether.

BACKGROUND OF THE INVENTION

Methanol is primarily used to produce formaldehyde, methyl tertiary butyl ether (MTBE) and acetic acid, with smaller amounts going into the manufacture of dimethyl terephthalate (DMT), methylmethacrylate (MMA), chloromethanes, methylamines, glycol methyl ethers, and fuels. It also has many general solvent and antifreeze uses, such as being a component for paint strippers, car windshield washer compounds and a de-icer for natural gas pipelines A major use of methyl acetate is as a low toxicity solvent in glues, paints and a broad range of coating and ink resin applications. Methyl acetate also finds use as a feedstock in the production of acetic anhydride.

Methanol may be produced on a commercial basis by the conversion of synthesis gas containing carbon monoxide, hydrogen and optionally carbon dioxide over a suitable catalyst according to the overall reaction:

Widely used catalysts for methanol synthesis from synthesis gas are based on copper.

WO 03/097523 describes a plant and process that produces methanol and acetic acid under substantially stoichiometric conditions, wherein an unadjusted syngas having an R ratio less than 2.0 is provided. All or part of the unadjusted syngas is supplied to a separator unit to recover $CO_2$, CO and hydrogen. At least a portion of any one or combination of the recovered $CO_2$, CO and hydrogen is added to any remaining syngas not so treated or alternatively combines in the absence of any remaining unadjusted syngas to yield an adjusted syngas with an R ratio of 2.0 to 2.9 which is used to produce methanol. Any recovered CO2 not used to adjust the R ratio of the unadjusted syngas can be supplied to the reformer to enhance CO production. At least a portion of the recovered CO is reacted in the acetic acid reactor with at least a portion of the produced methanol to produce acetic acid or an acetic acid precursor by a conventional process.

Methyl acetate may be produced by an integrated process as described in EP-A-0529868, in which process methanol and acetic acid are reacted in an esterification reactor and the methyl acetate is recovered by distillation and the water by azeotropic distillation, the process is operated in 'standby' mode by shutting off the methanol and acetic acid feds to the esterification reactor and recycling the methyl acetate and water to the esterification reactor so that the process may be rapidly restarted.

Methyl acetate may be produced, as described, for example in WO 2006/121778, by carbonylating dimethyl ether with carbon monoxide in the presence of a zeolite carbonylation catalyst, such as a mordenite zeolite.

The production of methyl acetate by the carbonylation of dimethyl ether may also be carried out using mixtures of carbon monoxide and hydrogen, as described, for example in WO 2008/132438. According to WO 2008/132438, the molar ratio of carbon monoxide:hydrogen for use in the carbonylation step may be in the range 1:3 to 15:1, such as 1:1 to 10:1, for example, 1:1 to 4:1.

WO 01/07393 describes a process for the catalytic conversion of a feedstock comprising carbon monoxide and hydrogen to produce at least one of an alcohol, ether and mixtures thereof and reacting carbon monoxide with the at least one of an alcohol, ether and mixtures thereof in the presence of a catalyst selected from solid super acids, heteropolyacids, clays, zeolites and molecular sieves, in the absence of a halide promoter, under conditions of temperature and pressure sufficient to produce at least one of an ester, acid, acid anhydride and mixtures thereof.

GB 1306863 describes a process for producing acetic acid, which comprises the following steps: (a) reacting a gaseous mixture of carbon monoxide and hydrogen in a molar ratio of 1:not more than 0.5, with methanol in the gas phase in the presence of a transition metal catalyst and a halogen-containing compound co-catalyst until no more than half of the carbon monoxide is consumed; (b) cooling the reacted gas obtained in step (a), separating the cooled gas into a liquid component containing acetic acid and a gaseous component containing unreacted carbon monoxide and hydrogen, and withdrawing the acetic acid from the reaction system; (c) washing the gaseous component from step (b) with cold methanol; and (d) reacting the washed gaseous component from step (c) in the presence of a copper-containing catalyst to yield methanol and passing this methanol to step (a).

U.S. Pat. No. 5,286,900 relates to a process for preparing an acetic acid product selected from acetic acid, methyl acetate, acetic anhydride and mixtures thereof by conversion of a synthesis gas comprising hydrogen and carbon oxides, said process comprising the steps of: (i) introducing synthesis gas into a first reactor at a pressure of 5-200 bar and a temperature of 150-400° C., and catalytically converting the synthesis gas into methanol and dimethyl ether and (ii) carbonylating the methanol and dimethyl ether formed in step (i) by passing the entire effluent from the first reactor to a second reactor and carbonylating therein, at a pressure of 1-800 bar and a temperature of 100-500° C. in the presence of a catalyst, the methanol and dimethyl ether to an acetic acid product.

EP-A-0801050 describes a process for the preparation of acetic acid which comprises catalytic steps of converting hydrogen and carbon monoxide in the synthesis gas to a mixed process stream containing methanol and dimethyl ether and carbonylating methanol and dimethyl ether formed in the process stream into acetic acid.

U.S. Pat. No. 5,502,243 describes a process wherein oxygenated acetyl compounds ethylidene acetate, acetic acid, acetic anhydride, acetaldehyde and methyl acetate are produced directly from synthesis gas and dimethyl ether in a catalyzed liquid phase reaction system. The inclusion of carbon dioxide in the synthesis gas in selected amounts increases the overall yield of oxygenated acetyl compounds from the reactant dimethyl ether. When methanol is included in the reactor feed, the addition of carbon dioxide significantly improves the molar selectivity to ethylidene diacetate.

EP-A-0566370 describes a process for the production of ethylidene diacetate, acetic acid, acetic anhydride and methyl acetate directly from synthesis gas via an intermediate product stream containing dimethyl ether. Dimethyl ether is produced from synthesis gas in a first liquid phase reactor and the reactor effluent comprising dimethyl ether, methanol and unreacted synthesis gas flows to a second liquid phase reactor containing acetic acid in which the oxygenated acetyl compounds are synthesized catalytically. Vinyl acetate and additional acetic acid optionally are produced by pyrolysis of ethylidene diacetate in a separate reactor system. Synthesis gas is preferably obtained by partial oxidation of a hydrocarbon feedstock such as natural gas. Optionally a portion of the acetic acid co-product is recycled to the partial oxidation reactor for conversion into additional synthesis gas.

Synthesis gas comprises carbon monoxide and hydrogen. Optionally carbon dioxide is included. The synthesis gas ratio or stoichiometric number (SN) of a synthesis gas composition is conventionally calculated as $$SN=(H_2-CO_2)/(CO+CO_2)$$

wherein $H_2$, CO and $CO_2$ represent the composition of the gas on a molar basis.

Desirably, the optimum stoichiometric number of a synthesis gas for use in methanol production is 2.05. Typically, however, processes for the production of methyl acetate by the carbonylation of dimethyl ether with synthesis gas employ synthesis gas with a stoichiometric excess of carbon monoxide. Thus a major drawback in integrated carbonylation and methanol synthesis processes is that the hydrogen:carbon monoxide ratios desirable for methanol synthesis are significantly higher than the desired ratios for carbonylation.

A further drawback of processes for the carbonylation of dimethyl ether is that a purge gas must be removed from the process to prevent recycle components from reaching unacceptable levels in the reactor. Typically, purge gases are disposed of by burning. Purge gas from the carbonylation process contains carbon monoxide and invariably contains some dimethyl ether and methyl acetate. Therefore, the removal of these components by purging represents a loss of values and reduces the overall efficiency of the process.

As described above, processes for the carbonylation of dimethyl ether with synthesis gas typically employ synthesis gas with a stoichiometric excess of carbon monoxide. This results in unconsumed carbon monoxide being withdrawn (together with hydrogen which generally remains unconsumed in the process) from the process as part of the carbonylation product stream. Typically, to avoid loss of carbon monoxide from the process it is recycled together with the unconsumed hydrogen to the carbonylation reactor. A disadvantage of this is that hydrogen builds-up in the reactor and an undesirable reduction in the carbonylation reaction rate is observed.

A yet further drawback is that the introduction of synthesis gas streams containing methyl acetate to methanol synthesis processes has now been found to result in undesirable side-reactions and/or by-products, such as ethanol and acetic acid resulting in a detrimental loss of catalytic performance and/or methanol productivity.

SUMMARY OF THE INVENTION

It has now been found that the above-described problems may be overcome or at least mitigated by integrating a process for the production of methyl acetate by the carbonylation of dimethyl ether with a methanol synthesis process wherein the carbonylation and methanol synthesis processes are operated with fresh synthesis gas feeds differing in stoichiometric number and the synthesis gas removed from the carbonylation process is usefully employed as a feed for methanol synthesis.

Accordingly, the present invention provides an integrated process for the production of methyl acetate and methanol which process comprises:

(i) supplying a first synthesis gas and dimethyl ether to a carbonylation reaction zone and reacting therein the dimethyl ether and the synthesis gas in the presence of a carbonylation catalyst to form a gaseous carbonylation reaction product comprising methyl acetate and a synthesis gas enriched in hydrogen;

(ii) withdrawing carbonylation reaction product from the carbonylation reaction zone and recovering therefrom a methyl acetate-rich liquid stream and a synthesis gas stream; and (iii) supplying at least a portion of the synthesis gas recovered from the carbonylation reaction product and a second synthesis gas to a methanol synthesis zone and contacting therein the synthesis gas with a methanol synthesis catalyst to form a methanol synthesis product comprising methanol and unconverted synthesis gas.

Advantageously, the present invention provides a process for the production of both methyl acetate and methanol from synthesis gas whilst minimizing loss of valuable carbon monoxide from methyl acetate production. Unreacted carbon monoxide and hydrogen present in the carbonylation reaction product is usefully converted to methanol in the methanol synthesis zone.

Advantageously, the present invention provides a process which allows for the reduction or complete elimination of the need to dispose of purge gas vented from a process for the carbonylation of dimethyl ether with carbon monoxide in the presence of a catalyst to produce methyl acetate.

Advantageously, the present invention provides a process which enhances zeolite carbonylation catalyst lifetime and/or catalytic performance by mitigating the build-up of recycle hydrogen.

Furthermore, the present invention allows the production of methanol whilst avoiding or mitigating the need for imported carbon dioxide thereby reducing methanol process costs.

BRIEF DESCRIPTION OF THE DRAWINGS

The accompanying drawings, which are incorporated in and constitute part of the specification, illustrate embodiments of the invention and, together with the description, serve to explain the features, advantages, and principles of the invention. In the drawings.

DETAILED DESCRIPTION OF THE INVENTION

Figure 1:
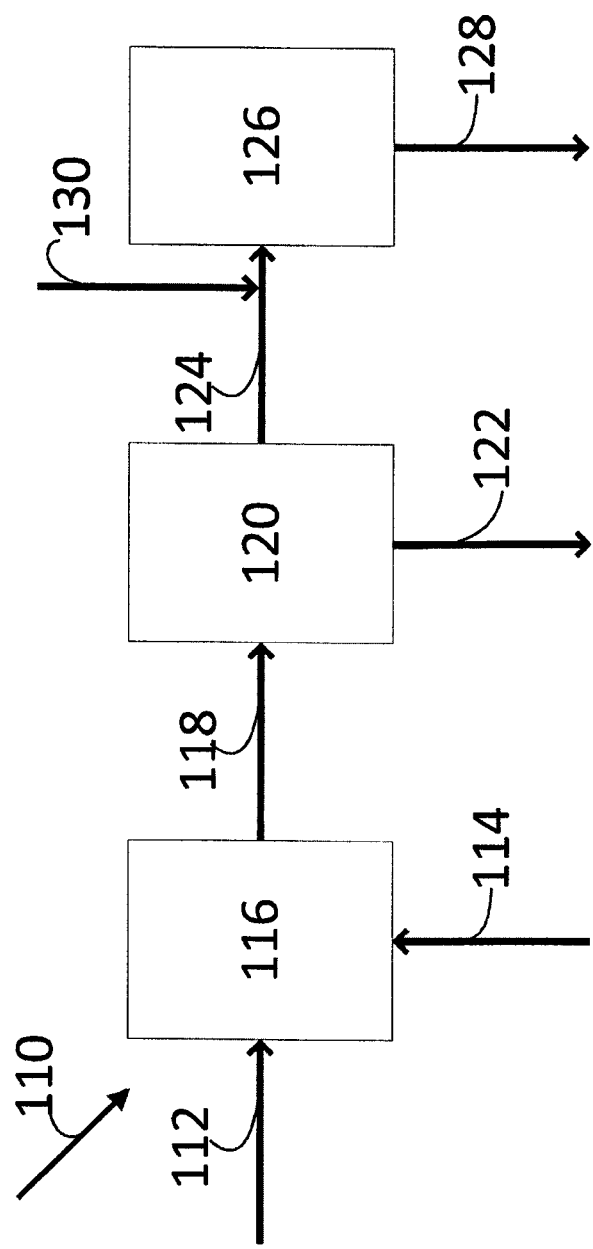
FIG. 1 is a block diagram showing one embodiment of the present invention of an integrated process for the production of methyl acetate and methanol.

As discussed above, synthesis gas comprises carbon monoxide and hydrogen. Optionally, synthesis gas may also comprise carbon dioxide. Typically, synthesis gas may also comprise small amounts of inert gases such nitrogen and methane. Conventional processes for converting hydrocarbon sources to synthesis gas include steam reforming and partial oxidation. Examples of hydrocarbon sources used in synthesis gas production include bio-mass, natural gas, methane, $C_2$-$C_5$ hydrocarbons, naphtha, coal and heavy petroleum oils.

Steam reforming generally comprises contacting a hydrocarbon with steam to form synthesis gas. The process preferably includes the use of a catalyst, such as those based on nickel.

Partial oxidation generally comprises contacting a hydrocarbon with oxygen or an oxygen-containing gas such as air to form synthesis gas. Partial oxidation takes place with or without the use of a catalyst, such as those based on rhodium, platinum or palladium.

Depending upon the nature of the hydrocarbon source used and the specific synthesis gas generation process employed, the stoichiometric number of the synthesis gas produced can vary. Typically, synthesis gas produced by steam reforming and partial oxidation of natural gas or methane has a stoichiometric number of at least 1.5 and is higher than, for example, synthesis gas produced by the gasification of coal, wherein the stoichiometric number may be 0.1 or less. In many instances, synthesis gas of various stoichiometric numbers is available within a synthesis gas facility.

In the present invention, dimethyl ether and a first synthesis gas comprising carbon monoxide and hydrogen is reacted in a carbonylation reaction zone in the presence of a suitable carbonylation catalyst to produce a gaseous carbonylation reaction product comprising methyl acetate and synthesis gas enriched in hydrogen. A second synthesis gas feed together with synthesis gas recovered from the carbonylation reaction product is contacted with a methanol synthesis catalyst to form a methanol synthesis product comprising methanol and unconverted synthesis gas.

Advantageously in the present invention the first synthesis gas for use in the carbonylation reaction may have a low stoichiometric number (SN). Preferably, the first synthesis gas has a stoichiometric number of 1.1 or less, for example in the range 0.05 to 1.1, such as in the range 1.0 to 1.1 (including any recycles). The second synthesis gas is of a composition such that a combination of the second synthesis gas and synthesis gas recovered from the carbonylation reaction product has a stoichiometric number which is higher than the stoichiometric number of the first synthesis gas. Suitably, the stoichiometric number of a combination of the second synthesis gas and synthesis gas recovered from the carbonylation reaction product is in the range 1.5 to 2.5, preferably in the range 2.0 to 2.1, more preferably 2.05.

Suitably at least one of the first and second synthesis gas comprises carbon dioxide. Carbon dioxide may be present in each of the first and second synthesis gas in an amount of not greater than 50 mol %, such as in the range 0.5 to 12 mol %.

Suitably, the first synthesis gas is cooled prior to being introduced to the carbonylation reaction zone. Preferably, the synthesis gas is cooled so as to condense at least a portion of the water vapour formed during the synthesis gas forming process.

The first synthesis gas supplied to the carbonylation reaction zone is preferably a dry synthesis gas. Water may be removed from the synthesis gas, using any suitable means, for example a molecular sieve.

The first synthesis gas may be fresh synthesis gas. For the present purposes, fresh synthesis gas includes stored sources of synthesis gas. Suitably, the first synthesis gas consists essentially of fresh synthesis gas that is in the absence of any recycle synthesis gas. Preferably, the fresh synthesis gas comprises carbon dioxide. The first synthesis gas to the carbonylation reaction zone may also comprise recycle synthesis gas. Recycle synthesis gas streams can be one or more gaseous or liquid streams comprising carbon monoxide, hydrogen and optionally carbon dioxide which are recovered from any part of the process downstream of the carbonylation reaction. Suitable recycle synthesis gas streams include synthesis gas recovered from the carbonylation reaction product.

In an embodiment, the first synthesis gas comprises a mixture of fresh synthesis gas and synthesis gas recovered from the carbonylation reaction product.

The first synthesis gas may be supplied to the carbonylation reaction zone as one or more feed streams. The one or more feed streams may be either fresh synthesis gas or a mixture of fresh and recycle synthesis gas.

Preferably, prior to use in the carbonylation reaction, the first synthesis gas (whether fresh or a mixture of fresh and recycle) is heated, for example in one or more heat exchangers, to the desired carbonylation reaction temperature.

The carbon monoxide partial pressure in the carbonylation reaction zone should be sufficient to permit the production of methyl acetate. Thus, suitably, the carbon monoxide partial pressure is in the range 0.1 to 100 barg (10 kPa to 10,000 kPa), such as 10 to 65 barg (1000 kPa to 6500 kPa).

The hydrogen partial pressure in the carbonylation reaction zone is suitably in the range 1 barg to 100 barg (100 kPa to 10,000 kPa), preferably 10 to 75 barg (1000 kPa to 7500 kPa).

The dimethyl ether for use in the carbonylation reaction may be fresh dimethyl ether or a mixture of fresh and recycle dimethyl ether. Suitably, recycle streams to the carbonylation reaction zone comprising dimethyl ether may be obtained from any part of the process downstream of the carbonylation reaction including, for example, the synthesis gas recovered from the carbonylation reaction product.

Dimethyl ether may be supplied to the carbonylation reaction zone as one or more fresh dimethyl ether streams or as one or more streams comprising a mixture of fresh and recycle dimethyl ether.

Dimethyl ether and the first synthesis gas may be supplied to the carbonylation reaction zone as one or more separate streams but preferably are introduced as one or more combined synthesis gas and dimethyl ether streams.

In an embodiment, the dimethyl ether and first synthesis gas is supplied to the carbonylation reaction zone as a combined stream, which combined stream is heated to the desired carbonylation reaction temperature, for example in one or more heat exchangers, prior to use in the carbonylation reaction zone.

In commercial practice, dimethyl ether is produced by the catalytic conversion of methanol over methanol dehydration catalysts. This catalytic conversion results in a product which is predominantly dimethyl ether but it may also contain low levels of methanol and/or water. The presence of significant amounts of water in a zeolite catalysed carbonylation of dimethyl ether tends to inhibit the production of methyl acetate product. In addition, water may be generated in the carbonylation reaction via side-reactions. However, the dimethyl ether for use in the carbonylation reaction of the present invention may contain small amounts of one or more of water and methanol provided that the total amount of methanol and water is not so great as to significantly inhibit the production of methyl acetate. Suitably, the dimethyl ether (including recycles) may contain water and methanol in a total amount in the range 1 ppm to 10 mol %, for example 1 ppm to 2 mol %, such as 1 ppm to 1 mol %, preferably in the range from 1 ppm to 0.5 mol %.

Preferably, the dimethyl ether (fresh and recycle) feed is dried prior to use in the carbonylation reaction.

The concentration of dimethyl ether may be in the range of 1 mol % to 20 mol %, suitably in the range 1.5 mol % to 15 mol %, for instance 5 to 15 mol %, for example 2.5 to 12 mol %, such as 2.5 to 7.5 mol % based on the total of all streams to the carbonylation reaction zone.

The molar ratio of carbon monoxide to dimethyl ether in the carbonylation reaction zone is suitably in the range 1:1 to 99:1, for example 1:1 to 25:1, such as 2:1 to 25:1.

Carbon dioxide reacts with hydrogen to form water and carbon monoxide. This reaction is commonly referred to as the reverse water gas shift reaction. Thus, where it is desired to utilise synthesis gas comprising carbon dioxide, to mitigate the effect of water on the carbonylation reaction, it is preferred that the carbonylation catalyst is not active for the reverse water-gas shift reaction or for the production of methanol. Preferably, the carbonylation catalyst comprises an aluminosilicate zeolite.

Zeolites comprise a system of channels which may be interconnected with other channel systems or cavities such as side-pockets or cages. The channel systems are defined by ring structures which rings may comprise, for example, 8, 10, or 12 members. Information about zeolites, their framework structure types and channel systems is published in the Atlas of Zeolite Framework Types, C. H. Baerlocher, L. B. Mccusker and D. H. Olson, 6th Revised Edition, Elsevier, Amsterdam, 2007 and is also available on the website of the International Zeolite Association at www.iza-online.org.

Suitably, the carbonylation catalyst is an aluminosilicate zeolite which comprises at least one channel which is defined by an 8-member ring. The aperture of the zeolite channel system defined by the 8-membered ring should be of such dimensions that the reactant dimethyl ether and carbon monoxide molecules can diffuse freely in and out of the zeolite framework. Suitably, the aperture of the 8-member ring channel of the zeolite has dimensions of at least 2.5×3.6 Angstroms. Preferably, the channel defined by the 8-member ring is interconnected with at least one channel defined by a ring with 10 or 12 members.

Non-limiting examples of aluminosilicate zeolites which comprise at least one channel which is defined by an 8-membered ring include zeolites of framework structure type MOR (for example, mordenite), FER (for example, ferrierite), OFF (for example, offretite) and GME (for example, gmelinite).

A preferred carbonylation catalyst is a mordenite zeolite.

The carbonylation catalyst may be a zeolite in its hydrogen form. Preferably, the carbonylation catalyst is mordenite in its hydrogen form.

The carbonylation catalyst may be a zeolite which is fully or partially loaded with one or more metals. Suitable metals for loading onto the zeolite include copper, silver, nickel, iridium, rhodium, platinum, palladium or cobalt and combinations thereof, preferably copper, silver and combinations thereof. The metal loaded form may be prepared by techniques such as ion-exchange and impregnation. These techniques are well-known and typically involve exchanging the hydrogen or hydrogen precursor cations (such as ammonium cations) of a zeolite with metal cations.

The carbonylation catalyst may be an aluminosilicate zeolite which, in addition to aluminium and silicon, has present in its framework one or more additional metals such as trivalent metals selected from at least one of gallium, boron and iron. Suitably, the carbonylation catalyst may be a zeolite which contains gallium as a framework element. More suitably, the carbonylation catalyst is a mordenite which contains gallium as a framework element, most suitably the carbonylation catalyst is a mordenite which contains gallium as a framework element and is in its hydrogen form.

The carbonylation catalyst may be a zeolite which is composited with at least one binder material. As will be appreciated by those of ordinary skilled in the art, binder materials are selected such that the catalyst is suitably active and robust under the carbonylation reaction conditions. Examples of suitable binder materials include inorganic oxides, such as silicas, aluminas, alumina-silicates, magnesium silicates, magnesium aluminium silicates, titanias and zirconias. Preferred binder materials include aluminas, alumina-silicates and silicas, for example boehemite type alumina.

The relative proportions of the zeolite and the binder material may vary widely but suitably, the binder material may be present in a composite in an amount in the range of 10% to 90% by weight of the composite, preferably in the range of 10% to 65% by weight of the composite.

Zeolite powders may also be formed into particles without the use of a binder. Typical zeolite catalyst particles include extrudates whose cross sections are circular or embrace a plurality of arcuate lobes extending outwardly from the central portion of the catalyst particles.

In an embodiment of the present invention, the carbonylation catalyst is a zeolite, such as a mordenite which is composited with at least one inorganic oxide binder material, which may suitably be selected from aluminas, silicas and alumina-silicates, and is utilised in the form of a shaped body, such as an extrudate. In particular, the carbonylation catalyst is a mordenite composited with an alumina, such as a boehmite alumina. The mordenite composited with the alumina may contain gallium as a framework element.

The silica to alumina molar ratio of the zeolites for use as carbonylation catalysts in the present invention is the bulk or overall ratio. This can be determined by any one of a number of chemical analysis techniques. Such techniques include x-ray fluorescence, atomic absorption and ICP (inductive coupled plasma). All will provide substantially the same silica to alumina molar ratio value.

The bulk silica to alumina molar ratio (herein also termed "SAR") of synthetic zeolites will vary. For example, the SAR of a zeolite, such as mordenite, may range from as low as 5 to over 90.

The SAR of a zeolite for use as a carbonylation catalyst in the present invention may suitably be in the range from 10:1 to 90:1, for example 20:1 to 60:1.

It is preferred that a zeolite carbonylation catalyst is activated immediately before use, typically by heating it at elevated temperature for at least one hour under flowing nitrogen, carbon monoxide, hydrogen or mixtures thereof.

Preferably, the carbonylation reaction is carried out under substantially anhydrous conditions. Suitably therefore, as discussed above, to limit the presence of water in the carbonylation reaction, all reactants, including fresh first synthesis gas, fresh dimethyl ether, any recycles thereof and the carbonylation catalyst are dried prior to use in the carbonylation reaction. Suitably, the combined amount of water and methanol (a source of water) present in the carbonylation reaction is limited to be in the range 1 ppm to 0.5 mol %, preferably in the range 1 ppm to 0.1 mol %, and most preferably in the range 1 ppm to 0.05 mol %. Desirably, the combined amount of water and methanol introduced into the carbonylation reaction zone is not more than 0.5 mol %, for example 0 to 0.5 mol %, such as 1 ppm to 0.5 mol %.

The carbonylation catalyst may be employed in a fixed bed carbonylation reaction zone, for example in the shape of pipes or tubes, where the dimethyl ether and synthesis gas feeds, typically in gaseous form are passed over or through the carbonylation catalyst.

The carbonylation reaction is carried out in the vapour phase.

The first synthesis gas and dimethyl ether are reacted in the presence of the carbonylation catalyst under reaction conditions effective to form a gaseous carbonylation reaction product comprising methyl acetate.

Preferably, the carbonylation reaction is carried out at a temperature in the range of 100° C. to 350° C., for example in the range 250° C. to 350° C.

Preferably, the carbonylation reaction is carried out at a total pressure in the range 1 to 200 barg (100 kPa to 20,000 kPa), for example 10 to 100 barg (1000 kPa to 10,000 kPa), such as 50 to 100 barg (5000 kPa to 10,000 kPa).

In an embodiment, the carbonylation reaction is carried out at temperatures in the range 250 to 350° C. and at total pressures in the range 50 to 100 barg (5000 kPa to 10,000 kPa).

In a preferred embodiment, the first synthesis gas and dimethyl ether, preferably containing water and methanol in not more than a combined amount in the range 1 ppm to 10 mol %, are reacted in the presence of a carbonylation catalyst, such as an aluminosilicate zeolite having at least one channel which is defined by an 8-membered ring, for example mordenite, preferably mordenite in its hydrogen form, at a temperature in the range 100° C. to 350° C. and at a total pressure in the range 10 to 100 barg (1000 kPa to 10,000 kPa) to form a gaseous carbonylation reaction product comprising methyl acetate and synthesis gas enriched in hydrogen.

The dimethyl ether and first synthesis gas (optionally comprising carbon dioxide and any recycles) may suitably be fed to the carbonylation reaction zone at a total gas hourly space velocity of flow of gas through the catalyst bed (GHSV) is in the range 500 to 40,000 $h^{-1}$, such as 2000 to 20,000 $h^{-1}$.

Preferably, the carbonylation reaction is carried out substantially in the absence of halides, such as iodide. By the term 'substantially' is meant that the halide, for example the total iodide, content of the feed streams to the carbonylation reaction zone is less than 500 ppm, preferably less than 100 ppm.

The hydrogen present in the first synthesis gas is essentially inactive in the carbonylation reaction and thus the synthesis gas withdrawn from the carbonylation reaction zone is enriched in hydrogen compared to the hydrogen content of the first synthesis gas.

The gaseous carbonylation reaction product withdrawn from the carbonylation reaction zone comprises methyl acetate and a synthesis gas enriched in hydrogen. Typically, the carbonylation reaction product will comprise additional components, such as one or more of unreacted dimethyl ether, water, methanol, and acetic acid.

Carbon dioxide present in the synthesis gas feed to the carbonylation reaction zone is largely unconsumed in the carbonylation reaction, and consequently the carbonylation reaction product will also comprise carbon dioxide.

The carbonylation reaction product is withdrawn from the carbonylation reaction zone in gaseous form.

In the present invention, a methyl acetate-rich liquid stream comprising methyl acetate and a synthesis gas stream are recovered from the carbonylation reaction product.

Suitably, the carbonylation reaction product is withdrawn from the carbonylation reaction zone and cooled and separated to recover a methyl acetate-rich liquid stream and a synthesis gas stream. The cooling of the carbonylation reaction product may be carried out using one or more heat exchange means, such as conventional heat exchangers, to cool the carbonylation reaction product to, for example, a temperature in the range of 50° C. or less, such as to a temperature in the range 40 to 50° C. The cooled carbonylation reaction product may be separated for example, in one or more gas/liquid separation means such as a knock-out drum or a tangential inlet drum, to recover a methyl acetate-rich liquid stream and a synthesis gas stream, The methyl acetate-rich liquid stream comprises mainly methyl acetate and may also comprise some unreacted dimethyl ether, acetic acid and dissolved synthesis gas.

Methyl acetate may be recovered from the methyl acetate-rich liquid stream, for example by distillation, and sold as such or used as a feedstock in downstream chemical processes.

In an embodiment methyl acetate is recovered from at least a portion of the methyl acetate-rich liquid stream and the recovered methyl acetate is converted to acetic acid, preferably by a hydrolysis process. Hydrolysis of the recovered methyl acetate may be carried out using known processes, such as catalytic distillation processes. Typically, in catalytic distillation processes for the hydrolysis of methyl acetate, methyl acetate is hydrolysed with water in a fixed-bed reactor employing an acidic catalyst, such as an acidic ion exchange resin or a zeolite, to produce a mixture comprising acetic acid and methanol from which acetic acid and methanol may be separated by distillation, in one or more distillation stages.

The synthesis gas stream recovered from the carbonylation reaction product may comprise additional components such as one or more of unreacted dimethyl ether, carbon dioxide, acetic acid and methyl acetate.

Preferably, a portion of the synthesis gas recovered from the carbonylation reaction product is recycled to the carbonylation reaction zone.

Suitably, the synthesis gas recovered from the carbonylation reaction product is split into two portions, wherein a first portion of the synthesis gas is supplied to the methanol synthesis zone and at least one other portion, which, for example equal to the first portion, is recycled to the carbonylation reaction zone. Preferably, however, the synthesis gas recovered from the carbonylation reaction product is split into a major portion and a minor portion. More preferably, the synthesis gas is split into a major portion and a minor portion wherein the major portion is recycled to the carbonylation reaction zone and the minor portion is supplied to the methanol synthesis zone.

Suitably the major portion is at least 50 mol % of the synthesis gas, such as in the range 75 to 99 mol %, for example 95 to 98 mol %. Suitably, the minor portion is less than 50 mol %, such as in the range 1 to 25 mol %, for example 2 to 5 mol %.

In one embodiment, 80 to 99 mol %, preferably 95 to 98 mol % of the synthesis gas is recycled to the carbonylation reaction zone and 1 to 20 mol %, preferably 2 to 5 mol %, of the synthesis gas is supplied to the methanol synthesis zone.

Suitably, the synthesis gas recovered from the carbonylation reaction product may be compressed, in one or more compressors, prior to recycle to the carbonylation reaction zone.

If desired, a portion of the synthesis gas from the carbonylation reaction product can be vented as purge gas but, preferably, substantially all of the recovered synthesis gas is supplied to the methanol synthesis zone or is recycled to the carbonylation reaction zone or a combination of both.

As discussed above the synthesis gas recovered from the carbonylation reaction product will typically contain residual amounts of methyl acetate. The presence of methyl acetate in methanol synthesis is undesirable as it can lead to the formation of unwanted by-products such as one or more of ethanol and acetic acid. Thus, it is desirable to reduce the methyl acetate content of synthesis gas supplied to a methanol synthesis zone.

The amount of methyl acetate present in the synthesis gas will vary but typically, the synthesis gas comprises methyl acetate in an amount in the range 0.1 to 5 mol %, for example 0.5 to 5 mol %, such as 0.5 to 2 mol %, for instance 0.5 to 1 mol %.

Thus, in a preferred embodiment of the present invention, at least a portion of the synthesis gas recovered from the carbonylation reaction product is scrubbed with a scrubbing solvent to reduce the methyl acetate content of the synthesis gas. If desired, all of the synthesis gas may be scrubbed.

Suitably, scrubbing of the synthesis gas to reduce the methyl acetate content thereof is conducted in a scrubbing zone which may contain one or more scrubbing units. A scrubbing unit is suitably of conventional design, for example a column or tower within which high surface area materials such as trays or packing, is arranged so as to enable intimate contact of the synthesis gas and the scrubbing solvent and to ensure good mass transfer between the gas and liquid phases. Desirably, scrubbing is performed by counter-current contact of the synthesis gas and the scrubbing solvent so that the synthesis gas will flow upwardly through the column or tower and the scrubbing solvent will flow downwardly through the column or tower.

Suitably, a liquid stream comprising the scrubbing solvent and methyl acetate is withdrawn from the lower portion of a scrubbing unit.

Synthesis gas depleted in methyl acetate content is suitably removed from the upper portion of a scrubbing unit.

The synthesis gas may be subjected to multiple scrubbing treatments. Each scrubbing may be conducted with the same or different scrubbing solvent.

Where the synthesis gas is subjected to more than one scrubbing treatment, such as two scrubbing treatments, the synthesis gas may be subjected to a first scrubbing by contacting the synthesis gas with a first scrubbing solvent to obtain a liquid solvent stream comprising methyl acetate and synthesis gas depleted in methyl acetate. The synthesis gas depleted in methyl acetate is subjected to a second scrubbing by contacting the synthesis gas depleted in methyl acetate with a second liquid scrubbing solvent to obtain a liquid solvent stream comprising methyl acetate and synthesis gas further depleted in methyl acetate.

Multiple scrubbing of the synthesis gas may and, generally does result in the liquid solvent streams from each scrubbing having a different composition. For example, where the scrubbing solvent comprises methanol, most of the methyl acetate present in the synthesis gas to be scrubbed will be absorbed by the scrubbing solvent in the first scrubbing treatment so that the liquid methanol stream from the first scrubbing will contain higher amounts of methyl acetate than the liquid methanol streams obtained from subsequent scrubbing treatments.

Liquid solvent streams from a first and any subsequent scrubbing may be combined to form a single liquid stream.

Preferably, the temperature of a scrubbing solvent on entry into the scrubbing zone is from −50° C. to 100° C., more preferably from 0° C. to 60° C., most preferably from 35° C. to 55° C.

The scrubbing solvent may be any solvent capable of absorbing methyl acetate. Preferably, the scrubbing solvent comprises methanol. The scrubbing solvent may be pure methanol. Alternatively, the scrubbing solvent may comprise a mixture of methanol and other components, such as a mixture of methanol and one or more of water and dimethyl ether. Mixtures of methanol and one or more of dimethyl ether and water for use as the scrubbing solvent may be obtained from the methanol synthesis product produced in the methanol synthesis reaction.

Suitably, the scrubbing solvent is selected from imported methanol, a methanol-rich stream recovered from the methanol synthesis product and mixtures thereof.

Suitably, all or a portion of a methanol-rich stream recovered from the methanol synthesis product is used as a scrubbing solvent.

Preferably, a scrubbing solvent which comprises a mixture of methanol and water contains water in an amount of less than 20 w/w %, more preferably less than 10 w/w %, and most preferably less than 5 w/w %.

Preferably, a scrubbing solvent which comprises a mixture of methanol and dimethyl ether contains dimethyl ether in an amount of less than 20 w/w %, more preferably less than 10 w/w %.

In some or all embodiments of the present invention, at least a portion of the synthesis gas recovered from the carbonylation reaction product is subjected to multiple scrubbing treatments, such as two or more scrubbing treatments, in one scrubbing unit with a liquid scrubbing solvent. Suitably, the liquid solvent employed in each scrubbing treatment comprises, and preferably consists of, a portion of the methanol-rich stream recovered from the methanol synthesis product.

Dimethyl ether and acetic acid which may be present in the synthesis gas recovered from the carbonylation reaction product are generally absorbed by methanol-containing scrubbing solvents and consequently these components are removed, together with methyl acetate, as part of the liquid methanol solvent stream.

The liquid solvent stream comprising absorbed methyl acetate may be subject to processing and/or purification steps to recover the scrubbing solvent therefrom.

Where scrubbing of the synthesis gas is carried out, it is preferred to remove at least 80%, preferably at least 90%, more preferably at least 95% and most preferably at least 99%, of the methyl acetate from the synthesis gas.

Suitably, synthesis gas supplied to the methanol synthesis zone comprises methyl acetate in an amount 0 to 1 mol %, such as 0 to less than 1 mol %.

Scrubbed synthesis gas can be directly supplied to a methanol synthesis zone for use therein.

The stoichiometric number of the synthesis gas recovered from the carbonylation reaction product will depend principally upon the stoichiometric number of the fresh synthesis gas supplied to the carbonylation reaction zone and the degree of conversion therein, but it may be adjusted by varying the amount of synthesis gas which is recovered from the carbonylation reaction product and recycled to the carbonylation reaction zone. The stoichiometric number of the synthesis gas recovered from the carbonylation reaction product may therefore be adjusted by altering one or more of these factors so that the combined stoichiometric number of synthesis gas recovered from the carbonylation reaction product and the second synthesis gas is optimal for methanol synthesis, that is, in the range 1.5 to 2.5, preferably in the range 2.0 to 2.1, more preferably 2.05. Suitably, the synthesis gas recovered from the carbonylation reaction product has a stoichiometric number in the range 0.1 to 3.0.

Scrubbing of the synthesis gas does not substantially alter the amounts of carbon monoxide, hydrogen and carbon dioxide contained therein. However, if one or more of carbon monoxide, hydrogen and carbon dioxide are present in the scrubbing solvent a portion of any such components may be released from the scrubbing solvent and form part of the scrubbed synthesis gas. In general however, the stoichiometric number of the scrubbed synthesis gas corresponds approximately to the stoichiometric number of the synthesis gas recovered from the carbonylation reaction product. Suitably, therefore a scrubbed synthesis gas has a stoichiometric number in the range 0.1 to 3.0. Preferably, the stoichiometric number of a scrubbed synthesis gas is such that the combined stoichiometric number of the scrubbed synthesis gas and a second synthesis gas feed is optimal for methanol synthesis, that is, in the range 1.5 to 2.5, preferably in the range 2.0 to 2.1, more preferably 2.05.

The methanol synthesis process used to manufacture the methanol product stream of the present invention can be any suitable process. Commercially, methanol is produced by the catalytic conversion of carbon monoxide and hydrogen according to the overall equation $CO+2H_2 \leftrightharpoons CH_3OH$. The reaction proceeds in accordance with the following reactions:

$$CO_2 + 3H_2 \leftrightharpoons CH_3OH + H_2O \quad (I)$$

$$H_2O + CO \leftrightharpoons CO_2 + H_2 \quad (II)$$

In the present invention, carbon monoxide and hydrogen required for the production of methanol in the methanol synthesis zone is obtained from the synthesis gas recovered from the carbonylation reaction product and a second synthesis gas feed. The synthesis gas recovered from the carbonylation reaction product and supplied to the methanol synthesis zone may be scrubbed or unscrubbed.

In a preferred embodiment, the process of the present invention further comprises the steps of:
(iv) withdrawing methanol synthesis product from the methanol synthesis zone and recovering therefrom a methanol-rich liquid stream and a synthesis gas stream; and
(v) recycling at least a portion of the synthesis gas stream recovered from the methanol synthesis product to the methanol synthesis zone.

The second synthesis gas supplied to the methanol synthesis zone is a fresh synthesis gas.

Prior to use in the methanol synthesis zone, the synthesis gas feeds to the methanol synthesis zone, such as the second synthesis gas, the synthesis gas recovered from the methanol synthesis product and the synthesis gas recovered from the carbonylation reaction product may be heated, for example in one or more heat exchangers, to the desired methanol synthesis temperature.

In order for the methanol synthesis to proceed favourably, the synthesis gas recovered from the methanol synthesis product and second synthesis gas is preferably compressed to the desired methanol synthesis pressure.

The second synthesis gas and the synthesis gas recovered from the carbonylation reaction product may be supplied to the methanol synthesis zone as separate feedstreams or, preferably as a single combined feed.

The synthesis of methanol requires a source of carbon dioxide. Sources of carbon dioxide include synthesis gas, carbon dioxide generated in-situ during methanol synthesis and imported carbon dioxide. Carbon dioxide can be generated in-situ from water formed in the methanol synthesis process and by the addition of water to the methanol synthesis. However, there are a number of disadvantages associated with the addition of water to methanol synthesis for in-situ generation of carbon dioxide, including the requirements for additional processing and the provision of a suitable source of water. However, if desired, at least one of water and imported carbon dioxide may be introduced into the methanol synthesis zone. Most desirably, however, all of the carbon dioxide required for methanol synthesis is obtained from one or more of the first synthesis gas and the second synthesis gas or from in-situ generation from water formed in the methanol synthesis process.

Carbon dioxide which is unconsumed in the methanol synthesis is withdrawn from the methanol synthesis zone as part of the methanol synthesis product. If desired, carbon dioxide may be recovered from the methanol synthesis product, for example, by conventional liquid/gas separation techniques.

In general, dimethyl ether does not take part in methanol synthesis and consequently, dimethyl ether which may be present in the synthesis gas supplied to the methanol synthesis zone is withdrawn from the methanol synthesis zone as part of the methanol synthesis product.

The methanol synthesis is accomplished in the presence of a methanol synthesis catalyst. The second synthesis gas feed and at least a portion of the synthesis gas recovered from the carbonylation reaction product, and optionally at least a portion of synthesis gas recovered from the methanol synthesis product, is contacted in the methanol synthesis zone with a methanol synthesis catalyst.

A number of catalysts active for methanol synthesis are known in the art and are also available commercially, for example, the Katalco™ series of catalysts available from Johnson Matthey plc. Typically the catalysts are based on copper and may also contain one or more additional metals such as zinc, magnesium and aluminium.

In one embodiment of this invention, the methanol synthesis catalyst comprises copper, zinc oxide and alumina.

The methanol synthesis catalyst may be employed in a fixed bed methanol synthesis zone, for example in the shape of pipes or tubes, where the second synthesis gas, the synthesis gas recovered from the carbonylation reaction product and optionally synthesis gas recovered from the methanol synthesis product are passed over or through the methanol synthesis catalyst.

Preferably, the methanol synthesis is carried out in the vapour phase.

The second synthesis gas and at least a portion of the synthesis gas recovered from the carbonylation reaction product and optionally synthesis gas recovered from the methanol synthesis product is contacted with the methanol synthesis catalyst under reaction conditions effective to effect the conversion of synthesis gas to form a methanol synthesis product comprising methanol and unconverted synthesis gas.

Suitably, methanol synthesis is carried out at a temperature of from 210° C. to 300° C., such as in the range 210° C. to 270° C. or 220° C. to 300° C., for example in the range 230° C. to 275° C.

Preferably, the methanol synthesis is carried out at a total pressure in the range 25 to 150 barg (2500 kPa to 15,000 kPa), for example in the range 50 to 100 barg (5000 kPa to 10,000 kPa).

Suitably, the methanol synthesis is carried out at a temperature in the range in the range 230° C. to 275° C. and at a total pressure in the range 50 to 100 barg (5000 kPa to 10,000 kPa).

In an embodiment of the present invention, methanol synthesis is carried out at a temperature of from 210° C. to 270° C. and at a total pressure in the range 50 to 100 barg (5000 kPa to 10,000 kPa).

In a preferred embodiment, the second synthesis gas and at least a portion of the synthesis gas recovered from the carbonylation reaction product, and optionally synthesis gas recovered from the methanol synthesis product, is contacted with a methanol synthesis catalyst based on copper, preferably a catalyst comprising copper, zinc and aluminium, at a temperature in the range 220° C. to 300° C. or in the range 210° C. to 270° C. and at a total pressure in the range 25 to 150 barg (2500 kPa to 15,000 kPa).

Suitably, the total gas hourly space velocity of the total feed to the methanol synthesis zone (including any recycle synthesis gas, water and any imported carbon dioxide) is in the range 500 to 40,000 $h^{-1}$.

Contacting of the second synthesis gas and synthesis gas recovered from the carbonylation reaction product and optionally synthesis gas recovered from the methanol synthesis product, with the methanol synthesis catalyst produces a methanol synthesis product comprising methanol and unconverted synthesis gas. Depending on the exact nature of components of the synthesis gas feeds, the methanol synthesis product may comprise additional components such as one or more of carbon dioxide, water and dimethyl ether.

The methanol synthesis product is withdrawn from the methanol synthesis zone, preferably in vapour form.

Methanol may be recovered from the withdrawn methanol synthesis product by known recovery techniques. Suitably, methanol may be recovered from at least a portion of the methanol synthesis product, for example, by reducing the temperature of the methanol synthesis product to generate a cooled methanol-synthesis gas mixture. Suitably, the temperature of the mixture is reduced to a temperature in the range 30 to 50° C., preferably in the range 35 to 45° C. The cooled methanol-synthesis gas mixture is separated to recover a liquid methanol-rich product stream and a gaseous synthesis gas stream.

Preferably, substantially all of the methanol synthesis product is separated to recover a methanol-rich liquid stream and a synthesis gas stream.

Separation of at least a portion of the methanol synthesis product may be carried out in one or more separation units. Each of the separation unit(s) may be of conventional design and may comprise one or more heat exchange means to cool the methanol synthesis product to condense out liquid methanol together with other condensable components such as water, from the methanol synthesis product and one or more gas/liquid separation means such as a knock-out drum or a tangential inlet drum, to separate the cooled methanol-synthesis gas mixture to recover a methanol-rich liquid stream and a gaseous synthesis gas stream.

Alternatively, separation of the methanol synthesis product may be carried out directly in the methanol synthesis zone, that is, by withdrawing from the methanol synthesis zone one or more gaseous streams comprising synthesis gas and one or more liquid streams rich in methanol.

The methanol-rich liquid stream may comprise small amounts of water, unreacted dimethyl ether and ethanol.

In an embodiment of the present invention, the methanol-rich liquid stream recovered from the methanol synthesis product may be used as a scrubbing solvent to remove methyl acetate from synthesis gas comprising methyl acetate. Advantageously, this avoids the need to import an additional supply of methanol or other suitable scrubbing solvent for use in a scrubbing zone.

Where multiple scrubbing treatments of the synthesis gas recovered from the carbonylation reaction product are conducted, the methanol-rich liquid stream supplied to a scrubbing zone may be divided and equal or unequal portions of the stream supplied to each of two or more scrubbing units in the scrubbing zone. For example, a minor portion of the methanol-rich liquid stream, such as >0 to 20%, may be supplied to a first scrubbing unit and a major portion of the stream, such as 80% to <100%, may be supplied to a second scrubbing unit.

Alternatively and/or additionally, methanol may be recovered from the methanol-rich liquid stream by conventional purification means, such as distillation, and sold as such or it may be used, for example, as a feedstock in a variety of chemical processes. For example, the methanol may be carbonylated with carbon monoxide in the presence of a Group VIII noble metal catalyst, such as rhodium, iridium or mixtures thereof to form acetic acid.

Alternatively, the methanol may be dehydrated in the presence of a suitable catalyst to form dimethyl ether. Suitable catalysts include aluminas, such as gamma-alumina.

Dimethyl ether present in the methanol-rich liquid stream may be recovered therefrom, for example by distillation. The recovered dimethyl ether may be recycled to the carbonylation reaction zone.

The synthesis gas recovered from the methanol synthesis product may comprise carbon dioxide.

Preferably, at least a portion of the synthesis gas recovered from the methanol synthesis product is recycled to the methanol synthesis zone. Suitably, 90% or more, such as 90 to 99%, of the synthesis gas may be recycled to the methanol synthesis zone.

If desired, to reduce the build-up of inert gases in the methanol synthesis zone, a portion of the synthesis gas recovered from the methanol synthesis product may be vented as a purge stream. Suitably, 1 to 10% of the synthesis gas recovered from the methanol synthesis product may be vented as a purge stream.

Suitably, in each of the carbonylation reaction zone and the methanol synthesis zone, the reaction is conducted as a heterogeneous vapour phase reaction.

The integrated process of the present invention and its component methyl acetate and methanol production processes may each be operated as a continuous process or as a batch process, preferably, the integrated process is operated as a continuous process.

FIG. 1 is a block diagram showing one embodiment of the present invention of an integrated process for the production of methyl acetate and methanol. The integrated unit 110 includes a first synthesis gas feed line 112 and a dimethyl ether feed line 114 connected to a carbonylation reactor 116. The carbonylation reactor 116 contains a fixed bed of carbonylation catalyst, for example a mordenite zeolite, preferably mordenite in its hydrogen form. In use, fresh synthesis gas is heated to the desired carbonylation reaction temperature and fed to the carbonylation reactor 116 via synthesis gas feed line 112. The synthesis gas comprises carbon monoxide, hydrogen and carbon dioxide and has a stoichiometric number, for example in the range 0.05 to 1.1. Dry dimethyl ether is fed to the carbonylation reactor 116 via dimethyl ether feed line 114. The dimethyl ether and synthesis gas are contacted with the catalyst in the carbonylation reactor 116 at a temperature in the range 250° C. to 350° C. and a total pressure in the range 10 to 100 barg (1000 kPa to 10,000 kPa) to form a gaseous carbonylation reaction product comprising methyl acetate and synthesis gas enriched in hydrogen. The carbonylation reaction product is withdrawn from the carbonylation reactor 116 via a carbonylation reaction product line 118, and fed to a separation unit 120 comprising, for example, a heat exchanger and knock-out drum. In separation unit 120, the carbonylation reaction product is cooled, preferably to a temperature in the range 40° C. to 50° C., and a methyl acetate-rich liquid stream and a synthesis gas stream are recovered from the separation unit 120. The methyl acetate-rich liquid stream is recovered from the separation unit 120 via a liquid product line 122. The synthesis gas stream is recovered from the separation unit 120 via a gaseous product line 124, heated in one or more heat exchangers (not shown) to the desired methanol synthesis temperature and supplied in its entirety to a methanol reactor 126. A second synthesis gas comprising carbon monoxide, hydrogen and carbon dioxide is supplied to the methanol reactor 126 via a second synthesis gas feed line 130. The stoichiometric number of the second synthesis gas is higher than that of the first synthesis gas. The second synthesis gas feed line 130 joins the gaseous fraction line 124 so that the synthesis gas recovered from the separation unit 120 is combined with the second synthesis gas prior to supply to the methanol synthesis reactor 126. The methanol synthesis reactor 126 contains a methanol synthesis catalyst, preferably a methanol synthesis catalyst comprising copper, such as a Katalco™ catalyst available from Johnson Matthey plc. The combined synthesis gas feed is converted in the methanol synthesis zone 126 under methanol synthesis conditions, for example at a temperature in the range 230° C. to 275° C. and a total pressure of 50 to 100 barg (5000 kPa to 10,000 kPa), to a methanol synthesis product comprising methanol and unconverted synthesis gas which methanol synthesis product is withdrawn from the methanol synthesis zone 126 via a methanol synthesis product line 128.

Figure 2:
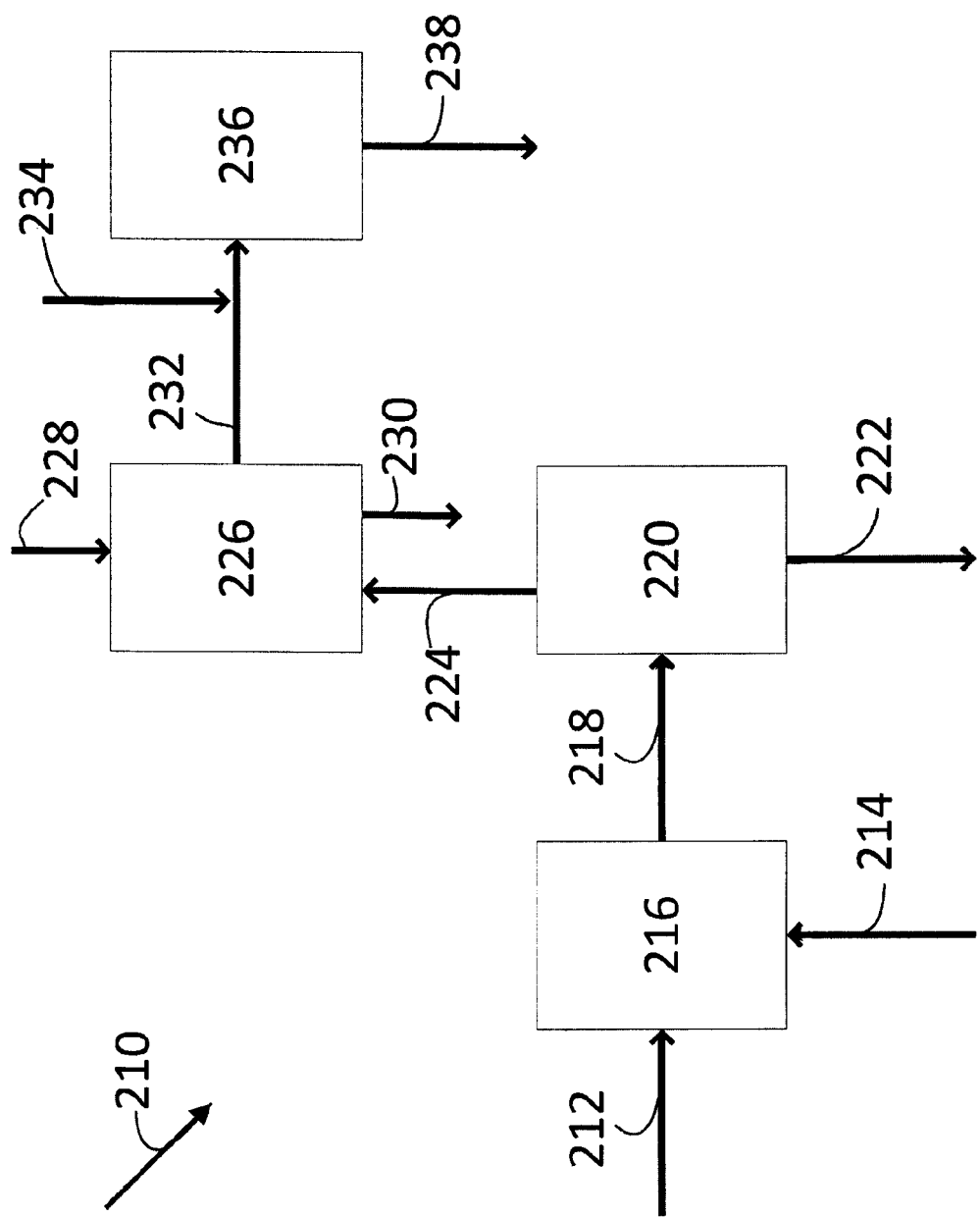
FIG. 2 is a block diagram showing an embodiment of the present invention of an integrated process for the production of methyl acetate and methanol and incorporating methanol product recovery.

FIG. 2 shows an integrated unit for the production of methyl acetate and methanol 210, according to an embodiment of the present invention. The integrated unit 210 includes a first synthesis gas feed line 212 and a dimethyl ether feed line 214 connected to a carbonylation reactor 216. The carbonylation reactor 216 contains a catalyst active for the carbonylation of dimethyl ether to methyl acetate, for example mordenite zeolite, preferably in its hydrogen form. In use, fresh synthesis gas is heated to the desired carbonylation reaction temperature and fed to the carbonylation reactor 216 via synthesis gas feed line 212. The synthesis gas having a stoichiometric number in the range 0.05 to 1.1 comprises carbon monoxide, hydrogen and carbon dioxide. Dry dimethyl ether is fed to the carbonylation reactor 216 via dimethyl ether feed line 214. The dimethyl ether and synthesis gas are contacted with the catalyst in the carbonylation reactor 216 at a temperature in the range 250° C. to 350° C. and a total pressure in the range 10 to 100 barg (1000 kPa to 10,000 kPa) to form a gaseous carbonylation reaction product comprising methyl acetate and synthesis gas enriched in hydrogen. The carbonylation reaction product is withdrawn from the carbonylation reactor 216 via a carbonylation reaction product line 218, and fed to a separation unit 220 comprising, for example, a heat exchanger and knock-out drum. In separation unit 220, the carbonylation reaction product is cooled, preferably to a temperature in the range 40° C. to 50° C., and a methyl acetate-rich liquid stream also comprising dimethyl ether and acetic acid, and a synthesis gas stream comprising small amounts of methyl acetate, dimethyl ether and acetic acid are recovered from the separation unit 220. The methyl acetate-rich liquid stream is recovered from the separation unit 220 via a liquid product line 222. The synthesis gas stream is recovered from the separation unit 220 via a gaseous product line 224 and supplied to a scrubbing unit 226. The scrubbing unit 226 is suitably supplied with a counter-current flow of liquid methanol via a methanol feed line 228, and the synthesis gas is contacted therein with the methanol to remove methyl acetate. Methanol containing absorbed methyl acetate is removed from the scrubbing unit 226 via a methanol removal line 230. The scrubbed synthesis gas depleted in methyl acetate is removed from the scrubbing unit 226 via a scrubbed synthesis gas line 232, heated in one or more heat exchangers (not shown) to the desired methanol synthesis temperature and supplied to a methanol synthesis reactor 236. A second synthesis gas comprising carbon monoxide, hydrogen and carbon dioxide is supplied to the methanol synthesis reactor 236 via second synthesis gas feed line 234. The stoichiometric number of the second synthesis gas is higher than the stoichiometric number of the first synthesis gas. The second synthesis gas feed line 234 joins the scrubbed synthesis gas line 232, so that the scrubbed synthesis gas is combined with the second synthesis gas before being supplied to the methanol synthesis reactor 236. The methanol synthesis reactor 236 contains a methanol synthesis catalyst, preferably a methanol synthesis catalyst comprising copper, such as a Katalco™ catalyst (ex Johnson Matthey plc). The combined synthesis gas feed is converted in the methanol synthesis reactor 236 under methanol synthesis conditions, for example at a temperature in the range 230° C. to 275° C. and a total pressure of 50 to 100 barg (5000 kPa to 10,000 kPa), to a methanol synthesis product comprising methanol and unconverted synthesis gas, which methanol synthesis product is withdrawn from the methanol synthesis reactor 236 via a methanol synthesis product line 238.

Figure 3:
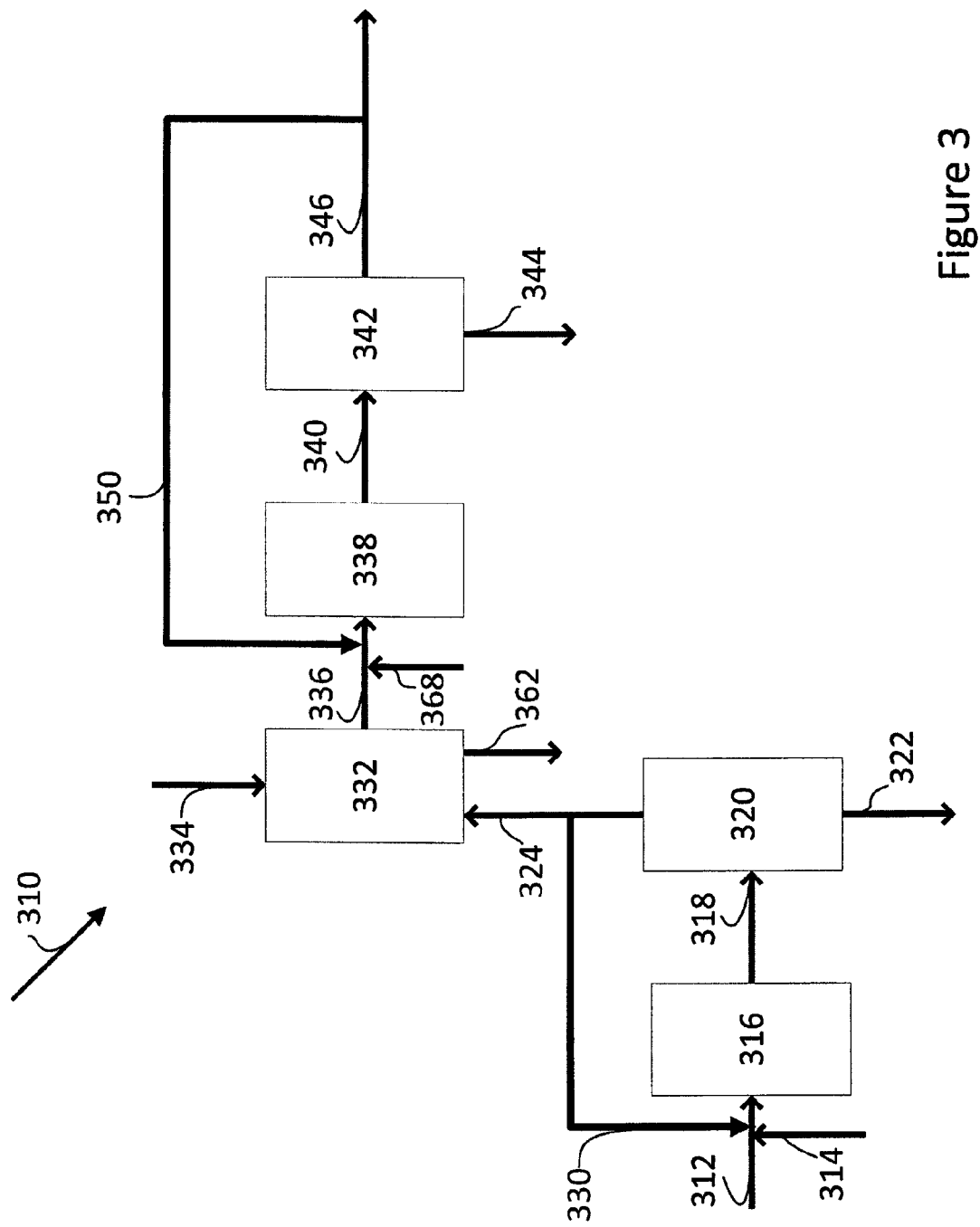
FIG. 3 is a block diagram showing an embodiment of the present invention of an integrated process for the production of methyl acetate and methanol and incorporating a methanol synthesis gas feed of fresh synthesis gas, scrubbed synthesis gas recovered from the carbonylation reaction product and synthesis gas recovered from the methanol synthesis product.

FIG. 3 shows an integrated unit for the production of methyl acetate and methanol 310 according to an embodiment of the present invention. The integrated unit 310 includes a first synthesis gas feed line 312 and a dimethyl ether feed line 314 connected to a carbonylation reactor 316. The carbonylation reactor 316 contains a catalyst active for the carbonylation of dimethyl ether to methyl acetate, for example mordenite zeolite, preferably in its hydrogen form. In use, fresh synthesis gas is heated to the desired carbonylation reaction temperature and fed to the carbonylation reactor 316 via synthesis gas feed line 312. The synthesis gas having a stoichiometric number in the range 0.05 to 1.1 comprises carbon monoxide, hydrogen and carbon dioxide. Dry dimethyl ether is fed to the carbonylation reactor 316 via dimethyl ether feed line 314. The dimethyl ether and synthesis gas are contacted with the catalyst in the carbonylation reactor 316 at a temperature in the range 250° C. to 350° C. and a total pressure in the range 10 to 100 barg (1000 kPa to 10,000 kPa) to form a gaseous carbonylation reaction product comprising methyl acetate and synthesis gas enriched in hydrogen. The carbonylation reaction product is withdrawn from the carbonylation reactor 316 via a carbonylation reaction product line 318, and fed to a first separation unit 320 comprising, for example, a heat exchanger and knock-out drum. In separation unit 320, the carbonylation reaction product is cooled, preferably to a temperature in the range 40° C. to 50° C., and a methyl acetate-rich liquid stream also comprising dimethyl ether, and a synthesis gas stream, are recovered from the separation unit 320. The methyl acetate-rich liquid stream is recovered from the separation unit 320 via a liquid product line 322. The synthesis gas stream is recovered from the separation unit 320 via a gaseous product line 324 and is split into a first portion and a second portion, for example by a suitable valve arrangement. The first portion of the synthesis gas, suitably comprising 2 to 5 mol % of the synthesis gas recovered from the carbonylation reaction product is supplied to a scrubbing unit 332. The second portion of the synthesis gas, suitably comprising 95 to 98 mol % of the synthesis gas recovered from the carbonylation reaction product, is recycled to the carbonylation reactor 316 via a first synthesis gas recycle line 330. The scrubbing unit 332 is supplied with a counter-current flow of liquid methanol via a methanol feed line 334, and the first portion of the synthesis gas is contacted with the methanol therein to remove methyl acetate from the synthesis gas. Methanol containing absorbed methyl acetate is removed from the scrubbing unit 332 via a methanol removal line 362, and the scrubbed synthesis gas is removed from the scrubbing unit via a scrubbed feed line 336. The scrubbed synthesis gas is supplied to a methanol synthesis reactor 338 via the scrubbed feed line 336. A second synthesis gas comprising carbon monoxide, hydrogen and carbon dioxide is supplied to the methanol synthesis reactor 338, via second synthesis gas feed line 368. The stoichiometric number of the second synthesis gas is higher than the stoichiometric number of the first synthesis gas. The second synthesis gas feed line 368 joins the scrubbed feed line 336, so that the scrubbed feed is combined with the second synthesis gas prior to supply to the methanol synthesis reactor 338. The methanol synthesis reactor 338 contains a methanol synthesis catalyst, preferably, a methanol synthesis catalyst comprising copper, such as a Katalco™ catalyst available from Johnson Matthey plc. The combined synthesis gas feed is converted in the methanol synthesis reactor 338 under methanol synthesis conditions, for example at a temperature in the range 230° C. to 275° C. and a total pressure of 50 to 100 barg (5000 kPa to 10,000 kPa), to a methanol synthesis product comprising methanol and unconverted synthesis gas, which methanol synthesis product is withdrawn from the methanol synthesis reactor 338 via a methanol synthesis product line 340 and is supplied to a second separation unit 342 which comprises, for example, a heat exchanger and a knock-out drum. The methanol synthesis product is cooled and separated in the second separation unit 342 to recover a methanol-rich liquid stream comprising methanol and water, and a synthesis gas stream. The methanol-rich liquid stream is removed from the second separation unit 342 via a methanol product line 344, and the synthesis gas is removed from the second separation unit 342 via a second synthesis gas line 346. The synthesis gas stream is divided, for example by a suitable valve arrangement, into a first portion suitably comprising 90 to 99% of the synthesis gas, and a second portion suitably comprising 1 to 10% of the synthesis gas. The first portion of the synthesis gas is recycled to the methanol synthesis reactor 338 via a second synthesis gas recycle line 350, which connects to the scrubbed feed line 336, so that the synthesis gas recovered from the methanol synthesis product is combined with the scrubbed synthesis gas and the second synthesis gas prior to supply to the methanol synthesis reactor 338. The second portion of the synthesis gas recovered from the methanol synthesis product is removed as a purge stream.

The invention is now illustrated with reference to the following non-limiting Examples.

EXAMPLE 1

This Example demonstrates an integrated process for the production of methyl acetate and methanol. FIG. 1 shows the basic components suitable for carrying out the integrated process of this Example.

A first synthesis gas comprising hydrogen, carbon monoxide and carbon dioxide with a hydrogen:carbon monoxide molar ratio of 0.83 and a stoichiometric number (SN) of 0.74, and comprising trace quantities of inert gases (First Syngas Feed), is fed to a carbonylation reactor. Dimethyl ether (DME Feed) is fed to the carbonylation reactor. The carbonylation reaction is conducted in the carbonylation reactor as a fixed bed vapour-phase process utilising H-mordenite zeolite as catalyst and is operated under conditions effective to catalyse the carbonylation of the dimethyl ether to produce methyl acetate, for example at a temperature in the range 250° C. to 350° C. and a total pressure in the range 10 to 100 barg (1000 kPa to 10,000 kPa). The gaseous carbonylation reaction product withdrawn from the carbonylation reactor comprises methyl acetate and synthesis gas enriched in hydrogen, is cooled and separated in a gas/liquid separator to recover a liquid stream rich in methyl acetate (Methyl Acetate Stream) and a gaseous stream comprising a synthesis gas (Syngas Feed (to methanol synthesis)). The synthesis gas stream has a stoichiometric number of 1.48. This synthesis gas stream is combined with a second synthesis gas (Second Syngas Feed) comprising hydrogen, carbon monoxide and carbon dioxide with a hydrogen:carbon monoxide molar ratio of 15.7 and a stoichiometric number of 9.2. The combined synthesis gas (Combined Feed) has a hydrogen:carbon monoxide molar ratio of 2.47 and a stoichiometric number of 2.04, and is heated to the methanol synthesis temperature and passed to a conventional methanol synthesis reactor. The synthesis is a low pressure synthesis operating at a total pressure of 50 to 100 barg (5000 kPa to 10,000 kPa), a temperature of from 240° C. to 275° C. and using a commercially available methanol synthesis catalyst comprising copper, such as a Katalco™ catalyst (ex Johnson Matthey plc), to produce a methanol synthesis product stream (Methanol Synthesis Product) comprising methanol and unconverted synthesis gas.

Examples of the molar flow rates that may be obtained in the above integrated process are given in Table 1 below.

TABLE 1

| Molar Flow per unit time | First Syngas Feed | DME Feed | Methyl Acetate Stream | Syngas Feed (to methanol) | Second Syngas feed | Combined Feed | Methanol Synthesis Product |
|---|---|---|---|---|---|---|---|
| Hydrogen | 1591 | | | 1591 | 771 | 2362 | 311 |
| Carbon monoxide | 1907 | | | 907 | 49 | 956 | 7 |
| Carbon dioxide | 102 | | | 102 | 32 | 134 | 83 |

TABLE 1-continued

| Molar Flow per unit time | First Syngas Feed | DME Feed | Methyl Acetate Stream | Syngas Feed (to methanol) | Second Syngas feed | Combined Feed | Methanol Synthesis Product |
|---|---|---|---|---|---|---|---|
| Inerts | 80 | | | 80 | 19 | 99 | 99 |
| Dimethyl ether | | 1000 | | | | | |
| Methyl acetate | | | 1000 | | | | |
| Methanol | | | | | | | 1000 |
| Hydrogen:carbon monoxide molar ratio | 0.83 | | | 1.75 | 15.7 | 2.47 | |
| Stoichiometric number (SN) | 0.74 | | | 1.48 | 9.2 | 2.04 | |

EXAMPLE 2

This Example demonstrates an integrated process for the production of methyl acetate and methanol, wherein a synthesis gas stream obtained from the carbonylation of dimethyl ether to produce methyl acetate is combined with fresh synthesis gas and the combined feed is used in methanol synthesis and wherein the product stream obtained from the methanol synthesis is separated into a methanol-rich liquid stream and a synthesis gas stream.

The process of Example 1 is repeated using a first synthesis gas (First Syngas Feed), a second synthesis gas (Second Syngas Feed) and a dimethyl ether feed (DME Feed) having the compositions set out in Table 2.

The product stream from the methanol synthesis reactor is supplied to a gas/liquid separation unit, comprising a heat exchanger and a knock-out drum, to recover a methanol-rich liquid stream (Methanol Product) and a synthesis gas stream (Syngas (from methanol)).

Examples of the molar flow rates that may be obtained in the above integrated process are given in Table 2 below.

TABLE 2

| Molar Flow per unit time | First Syngas Feed | DME Feed | Methyl Acetate Stream | Syngas feed (to methanol) | Second Syngas Feed | Combined Feed | Methanol Product | Syngas (from methanol) |
|---|---|---|---|---|---|---|---|---|
| Hydrogen | 1591 | | | 1591 | 771 | 2362 | | 311 |
| Carbon monoxide | 1907 | | | 907 | 49 | 956 | | 7 |
| Carbon dioxide | 102 | | | 102 | 32 | 134 | | 83 |
| Inerts | 80 | | | 80 | 19 | 99 | | 99 |
| Dimethyl ether | | 1000 | | | | | | |
| Methyl acetate | | | 1000 | | | | | |
| Methanol | | | | | | | 1000 | |
| Hydrogen:carbon monoxide molar ratio | 0.83 | | | 1.75 | 15.7 | 2.47 | | 42 |
| Stoichiometric number (SN) | 0.74 | | | 1.48 | 9.2 | 2.04 | | 2.53 |

EXAMPLE 3

This Example demonstrates an integrated process for the production of methyl acetate and methanol, wherein a synthesis gas stream obtained from the carbonylation of dimethyl ether to produce methyl acetate is used in combination with a fresh synthesis gas as the feed for methanol synthesis. FIG. 2 shows the basic components suitable for carrying out the integrated process of this Example.

A first synthesis gas comprising hydrogen, carbon monoxide and carbon dioxide with a hydrogen:carbon monoxide molar ratio of 0.83 and a stoichiometric number (SN) of 0.74, and comprising trace quantities of inert gases (First Synthesis Gas Feed), is supplied to the carbonylation reactor. A dry dimethyl ether feed (DME Feed) is also supplied to the carbonylation reactor. The carbonylation reactor is operated under conditions effective to catalyse the carbonylation of dimethyl ether to produce a product stream comprising methyl acetate, for example at a temperature in the range 250° C. to 350° C. and a pressure of 10 to 100 barg (1000 kPa to 10,000 kPa). The product stream from the carbonylation reactor is supplied to a gas/liquid separator and cooled and separated into a liquid stream comprising mainly methyl acetate, together with dimethyl ether, methanol, water and acetic acid (Carbonylation Product), and a synthesis gas stream comprising unreacted dimethyl ether methyl acetate and a trace amount of acetic acid (Synthesis Gas (from carbonylation)). The synthesis gas has a stoichiometric number of 1.46. The synthesis gas is supplied to a conventional gas/liquid scrubbing apparatus where it is counter-currently contacted with liquid solvent comprising methanol to remove methyl acetate, dimethyl ether and acetic acid. The scrubbed synthesis gas stream (the Scrubbed Synthesis Gas) has a reduced methyl acetate, dimethyl ether and acetic acid content, and a stoichiometric number of 1.48. The scrubbed synthesis gas is combined with a second synthesis gas (the Second Synthesis Gas Feed) comprising hydrogen, carbon monoxide and carbon dioxide with a hydrogen:carbon monoxide molar ratio of 15.74 and a stoichiometric number of 9.15. The combined scrubbed synthesis gas and second synthesis gas (the Combined Feed) has a hydrogen:carbon monoxide ratio of 2.45 and a stoichiometric number of 2.06, and is supplied to a conventional methanol synthesis reaction system, where it is contacted with a commercially available copper-containing methanol synthesis catalyst, such as a Katalco™ catalyst available from Johnson Matthey plc. The methanol synthesis reaction system is operated under conventional methanol synthesis reaction conditions, such as at a temperature of from 240° C. to 275° C. and a pressure of 50 to 100 barg (5000 kPa to 10,000 kPa), so as to produce a gaseous product stream (the Methanol Reactor Stream) comprising methanol, unconverted synthesis gas, water and dimethyl ether.

Examples of the molar flow rates that may be obtained in the above integrated process are given in Table 3 below.

of the gaseous stream (Recycle Synthesis gas (to carb)) being recycled to the carbonylation reactor to produce a combined feed (Total Synthesis Gas (to carb)), and approximately 3.2% of the synthesis gas stream (Scrubber Synthesis Gas) being diverted to a conventional gas/liquid scrubbing unit (such as a scrubbing column or tower) where it is contacted counter-currently with liquid solvent comprising methanol to remove methyl acetate and dimethyl ether. The scrubbed synthesis gas (Scrubbed Synthesis Gas) recovered from the scrubbing unit has a reduced methyl acetate and dimethyl ether content. The stoichiometric number of the scrubbed synthesis gas is 0.19. The scrubbed synthesis gas is combined with a second synthesis gas (Second Syngas

TABLE 3

| Molar Flow per unit time | First Synthesis Gas Feed | DME Feed | Carb. Product | Synthesis Gas (from carb) | Scrubbed Synthesis Gas | Second Synthesis Gas Feed | Combined Feed | Methanol Reactor Stream |
|---|---|---|---|---|---|---|---|---|
| Hydrogen | 1590.7 | 0.0 | 4.0 | 1546.7 | 1537.9 | 771.4 | 2309.3 | 249.8 |
| Methane | 3.6 | 0.0 | 0.6 | 43.1 | 42.5 | 0.0 | 42.5 | 42.5 |
| Nitrogen | 80.1 | 0.0 | 0.4 | 79.7 | 79.4 | 18.9 | 98.3 | 98.3 |
| Carbon monoxide | 1907.4 | 0.0 | 4.9 | 902.5 | 894.9 | 49.0 | 943.9 | 3.4 |
| Water | 0.0 | 0.2 | 2.5 | 1.6 | 1.1 | 0.0 | 1.1 | 60.6 |
| Carbon dioxide | 101.9 | 0.0 | 8.3 | 93.6 | 86.1 | 31.8 | 117.9 | 58.4 |
| Methanol | 0.0 | 1.5 | 14.9 | 2.7 | 31.9 | 0.0 | 31.9 | 1031.9 |
| Methyl acetate | 0.0 | 0.0 | 827.0 | 157.1 | 0.0 | 0.0 | 0.0 | 0.0 |
| Dimethyl ether | 0.0 | 1500.0 | 161.6 | 318.4 | 93.6 | 0.0 | 93.6 | 93.6 |
| Acetic acid | 0.0 | 0.0 | 15.6 | 0.4 | 0.0 | 0.0 | 0.0 | 0.0 |
| Total | 3683.7 | 1501.7 | 1039.8 | 3145.8 | 2767.4 | 871.1 | 3638.5 | 1638.5 |
| $H_2$:CO | 0.83 | | | 1.71 | 1.72 | 15.74 | 2.45 | |
| Stoichiometric number (SN) | 0.74 | | | 1.46 | 1.48 | 9.15 | 2.06 | |

EXAMPLE 4

This Example demonstrates an integrated process for the production of methyl acetate and methanol, wherein part of the synthesis gas obtained from the carbonylation of dimethyl ether to produce methyl acetate is scrubbed and used in combination with fresh synthesis gas and synthesis gas recovered from the methanol synthesis product as the feed for methanol synthesis. FIG. 3 shows the basic components suitable for carrying out the integrated process of this Example.

A first synthesis gas feed (First Syngas Feed) and a dimethyl ether feed (DME Feed) have the compositions set out in Table 4. The first synthesis gas feed has a hydrogen:carbon monoxide molar ratio of 0.10 and a stoichiometric number (SN) of 0.08. The synthesis gas and the dimethyl ether feed are combined before being supplied to the carbonylation reactor and reacted therein in the presence of a carbonylation catalyst, suitably a mordenite, preferably mordenite in its hydrogen form, at a temperature in the range 250° C. to 350° C. and at a total pressure in the range 10 to 100 barg (1000 kPa to 10,000 kPa), to form a carbonylation product stream comprising methyl acetate and synthesis gas enriched in hydrogen. The product stream from the carbonylation reactor (Carb Reaction Product) is withdrawn and supplied to a gas/liquid separator, wherein it is cooled and separated to recover a liquid stream comprising mainly methyl acetate (Methyl Acetate Liquid Stream), and a synthesis gas stream comprising unreacted dimethyl ether and methyl acetate (Synthesis gas (from carb)). The stoichiometric number of the synthesis gas is 0.22. The synthesis gas stream is split into two streams, with approximately 96.8%

Feed). The second synthesis gas has a stoichiometric number of 3.48, and the combined scrubbed synthesis gas and second synthesis gas (Combined Synthesis Gas) has a hydrogen:carbon monoxide molar ratio of 3.16 and a stoichiometric number of 2.05. The combined synthesis gas is supplied to a conventional methanol synthesis reactor in combination with a recycle stream (Recycle Synthesis Gas (from methanol)) recovered from the methanol synthesis product, to form a combined feed (Total Synthesis Gas Feed (to methanol)). The total synthesis gas supplied to the methanol synthesis reactor is contacted with a commercially available copper-containing methanol synthesis catalyst, such as a Katalco™ catalyst, available from Johnson Matthey plc. The methanol synthesis is operated under conventional methanol synthesis reaction conditions, such as at a temperature of from 230° C. to 275° C. and a pressure of 50 to 100 barg (5000 kPa to 10,000 kPa), so as to produce a methanol synthesis product comprising methanol (Methanol Synthesis Product). The product stream from the methanol synthesis is supplied to a conventional gas/liquid separation unit comprising a heat exchanger and a knockout drum, cooled and separated into a liquid stream comprising mainly methanol (Methanol Liquid Stream) and a synthesis gas stream (Synthesis Gas (from methanol)). Approximately 5% of this synthesis gas stream is vented as a purge gas (Methanol Purge) and the remainder (approximately 98%) of the synthesis gas stream is recycled to the methanol synthesis reactor (Recycle Synthesis Gas (from methanol)).

Examples of the molar flow rates that may be obtained in the above combined process are given in Table 4 below.

TABLE 4

| Molar Flow per unit time | First Syngas Feed | DME Feed | Recycle Synthesis Gas (to carb) | Total Synthesis Gas (to carb) | Carb Reaction Product | Methyl Acetate Liquid Stream | Synthesis Gas (from carb) | Scrubber Synthesis Gas | Scrubbed Synthesis Gas |
|---|---|---|---|---|---|---|---|---|---|
| $H_2$ | 15.2 | 0 | 309.5 | 324.7 | 320.6 | 0.84 | 319.8 | 10.3 | 10.8 |
| $CH_4$ | 0.1 | 0 | 88.4 | 88.5 | 92.5 | 1.2 | 91.3 | 2.9 | 3.2 |
| $N_2$ | 4.5 | 0 | 119.2 | 123.7 | 123.7 | 0.6 | 123.2 | 4.0 | 4.1 |
| CO | 151.5 | 0 | 1323.8 | 1475.3 | 1375.3 | 7.4 | 1367.9 | 44.1 | 43.8 |
| $H_2O$ | 0 | 0 | 1.2 | 1.2 | 3.2 | 2.0 | 1.2 | 0 | 0.4 |
| $CO_2$ | 2.5 | 0 | 20.2 | 22.7 | 22.7 | 1.8 | 20.9 | 0.7 | 1.9 |
| MeOH | 0 | 0.1 | 0 | 0.1 | 0.1 | 0.1 | 0 | 0 | 3.4 |
| MeOAC | 0 | 0 | 18.3 | 18.3 | 118.3 | 99.4 | 18.9 | 0.6 | 0 |
| DME | 0 | 121.5 | 35.0 | 156.5 | 54.5 | 18.3 | 36.2 | 1.2 | 0.4 |
| Total | 173.8 | 121.6 | 1915.6 | 2211.0 | 2110.9 | 131.6 | 1979.4 | 63.8 | 68.0 |
| $H_2$:CO | 0.10 | | 0.23 | 0.22 | 0.23 | | 0.23 | | 0.25 |
| SN | 0.08 | | 0.22 | 0.20 | 0.21 | | 0.22 | | 0.19 |

| Molar Flow per unit time | Second Syngas Feed | Combined Synthesis Gas | Recycle Synthesis Gas (from methanol) | Total Synthesis Gas (to methanol) | Methanol Synthesis Product | Methanol Liquid Stream | Synthesis Gas (from methanol) | Methanol Purge |
|---|---|---|---|---|---|---|---|---|
| $H_2$ | 233.3 | 244.1 | 362.4 | 606.5 | 383.0 | 0.5 | 382.5 | 20.1 |
| $CH_4$ | 0 | 3.2 | 51.9 | 55.1 | 55.1 | 0.3 | 54.8 | 2.9 |
| $N_2$ | 1.1 | 5.2 | 90.0 | 95.2 | 95.2 | 0.1 | 95.1 | 5.1 |
| CO | 33.5 | 77.3 | 11.9 | 89.2 | 12.6 | 0 | 12.6 | 0.7 |
| $H_2O$ | 0 | 0.4 | 1.0 | 1.4 | 24.8 | 23.8 | 1.0 | 0 |
| $CO_2$ | 26.1 | 28.0 | 57.4 | 85.4 | 62.0 | 1.4 | 60.6 | 3.2 |
| MeOH | 0 | 3.4 | 8.2 | 11.6 | 111.6 | 103.0 | 8.6 | 0.4 |
| MeOAC | 0 | 0 | 0 | 0 | 0 | 0 | 0 | 0 |
| DME | 0 | 0.4 | 0.9 | 1.3 | 1.3 | 0.4 | 0.9 | 0 |
| Total | 294.0 | 362.0 | 583.7 | 945.7 | 745.6 | 129.5 | 616.1 | 32.4 |
| $H_2$:CO | 6.96 | 3.16 | 30.45 | 6.80 | | | | |
| SN | 3.48 | 2.05 | 4.40 | 2.98 | | | | |

The abbreviations used in Table 4 have the following meanings:
DME is dimethyl ether
MeOH is methanol
MeOAc is methyl acetate
SN is stoichiometric number

EXAMPLE 5

This Example demonstrates an integrated process for the production of methyl acetate and methanol, wherein a synthesis gas stream obtained from the carbonylation of dimethyl ether to produce methyl acetate is used in combination with a fresh synthesis gas as the feed to the methanol synthesis reaction and wherein the product stream obtained from the methanol synthesis reaction system is separated into a methanol-rich liquid stream and a synthesis gas stream.

The process of Example 1 is repeated using a first synthesis gas (First Synthesis Gas Feed), a second synthesis gas (Second Synthesis Gas Feed) and a dimethyl ether feed (DME Feed) having the compositions set out in Table 5.

The product stream from the methanol synthesis reactor is supplied to a gas/liquid separation unit, comprising a heat exchanger and a knock-out drum, and cooled and separated to recover a liquid stream comprising mainly methanol (Methanol Product) and a synthesis gas stream (Synthesis gas (from methanol)) comprising methanol and dimethyl ether.

Examples of the molar flow rates that may be obtained in the above integrated process are given in Table 5 below.

TABLE 5

| Molar Flow per unit time | First Synthesis Gas Feed | DME Feed | Methyl Acetate Stream | Synthesis Gas (from Carb) | Scrubbed Synthesis Gas | Second Synthesis Gas Feed | Combined Feed | Methanol Product | Synthesis Gas (from methanol) |
|---|---|---|---|---|---|---|---|---|---|
| Hydrogen | 1590.7 | 0.0 | 4.0 | 1546.7 | 1537.9 | 771.4 | 2309.3 | 0.3 | 249.5 |
| Methane | 3.6 | 0.0 | 0.6 | 43.1 | 42.5 | 0.0 | 42.5 | 0.2 | 42.3 |
| Nitrogen | 80.1 | 0.0 | 0.4 | 79.7 | 79.4 | 18.9 | 98.3 | 0.1 | 98.2 |
| Carbon monoxide | 1907.4 | 0.0 | 4.9 | 902.5 | 894.9 | 49.0 | 943.9 | 0.0 | 3.4 |
| Water | 0.0 | 0.2 | 2.5 | 1.6 | 1.1 | 0.0 | 1.1 | 58.1 | 2.5 |
| Carbon dioxide | 101.9 | 0.0 | 8.3 | 93.6 | 86.1 | 31.8 | 117.9 | 1.3 | 57.1 |
| Methanol | 0.0 | 1.5 | 14.9 | 2.7 | 31.9 | 0.0 | 31.9 | 952.0 | 79.9 |
| Methyl acetate | 0.0 | 0.0 | 827.0 | 157.1 | 0.0 | 0.0 | 0.0 | 0.0 | 0.0 |

TABLE 5-continued

| Molar Flow per unit time | First Synthesis Gas Feed | DME Feed | Methyl Acetate Stream | Synthesis Gas (from Carb) | Scrubbed Synthesis Gas | Second Synthesis Gas Feed | Combined Feed | Methanol Product | Synthesis Gas (from methanol) |
|---|---|---|---|---|---|---|---|---|---|
| Dimethyl ether | 0.0 | 1500.0 | 161.6 | 318.4 | 93.6 | 0.0 | 93.6 | 26.1 | 67.5 |
| Acetic acid | 0.0 | 0.0 | 15.6 | 0.4 | 0.0 | 0.0 | 0.0 | 0.0 | 0.0 |
| Total | 3683.7 | 1501.7 | 1039.8 | 3145.8 | 2767.4 | 871.1 | 3638.5 | 1038.1 | 600.4 |
| $H_2$:CO | 0.83 | | | 1.71 | 1.72 | 15.74 | 2.45 | | |
| Stoichiometric number (SN) | 0.74 | | | 1.46 | 1.48 | 9.15 | 2.06 | | |

EXAMPLE 6

This Example investigates the effect of methyl acetate on methanol synthesis from synthesis gas. Pellets of Katalco™ methanol catalyst (Johnson Matthey plc) were crushed and sieved to a size-fraction of 125-160 microns. A tubular reactor of 9 mm internal diameter was charged with 3 ml of the catalyst diluted 1:1 v/v with quartz chips. The length of the catalyst bed was 100 mm. In Runs 1, 3, 4 and 6, synthesis gas of composition 62 mol % $H_2$, 7 mol % CO, 5 mol % $CO_2$, 21 mol % $N_2$ and 5 mol % Ar was fed to the reactor at total gas hourly space velocities (GHSV) of 5000 $h^{-1}$ and 20000 $h^{-1}$ under conditions of a total pressure of 75 bar (7500 kPa) and a temperature of 260° C. The experiments were repeated in Runs 2 and 5 using synthesis gas of composition 62 mol % $H_2$, 7 mol % CO, 5 mol % $CO_2$, 20 mol % $N_2$ and 5 mol % Ar and a co-feed of 1 mol % methyl acetate. In each experiment the exit stream from the reactor was passed to two gas chromatographs (GC's) for analysis of the components of the exit stream. The GC's were a Varian 4900 micro GC with three columns (molecular sieve 5A, Porapak®Q and CP-Wax-52), each column equipped with a thermal conductivity detector and an Interscience trace GC with two columns (CP Sil 5 and CP-Wax-52), each column equipped with a flame ionization detector. Table 5 below provides the space time yields (STY) in grams of methanol product per liter of catalyst per hour and selectivities (Sel) to methanol achieved for each of the experiments. The data in Table 6 clearly demonstrates that the production of methanol from synthesis gas is adversely affected by the presence of methyl acetate.

TABLE 6

| Run No. | Methyl acetate/ mol % | Temp/ ° C. | Time on stream/ hrs | GHSV/ $h^{-1}$ | Sel/% | STY/ g/l · h |
|---|---|---|---|---|---|---|
| 1 | 0 | 260 | 74 | 20000 | 99.9 | 1335 |
| 2 | 1 | 260 | 51 | 20000 | 95.7 | 803 |
| 3 | 0 | 260 | 44 | 20000 | 99.9 | 1041 |
| 4 | 0 | 260 | 74 | 5000 | 99.0 | 407 |
| 5 | 1 | 260 | 51 | 5000 | 96.0 | 364 |
| 6 | 0 | 260 | 44 | 5000 | 99.0 | 409 |

The invention claimed is:

1. An integrated process for the production of methyl acetate and methanol which process comprises:
   (i) supplying a first synthesis gas and dimethyl ether to a carbonylation reaction zone and reacting therein the dimethyl ether and the synthesis gas in the presence of a carbonylation catalyst to form a gaseous carbonylation reaction product comprising methyl acetate and a synthesis gas enriched in hydrogen gas relative to the hydrogen content of the feed synthesis gas and wherein the carbonylation catalyst is an aluminosilicate zeolite which comprises at least one channel which is defined by an 8-membered ring;
   (ii) withdrawing carbonylation reaction product from the carbonylation reaction zone and recovering therefrom a methyl acetate-rich liquid stream and a synthesis gas stream which synthesis gas stream is split into a major portion and a minor portion and wherein the major portion is recycled to the carbonylation reaction zone and the minor portion is scrubbed with a scrubbing solvent; and
   (iii) supplying the minor portion of the synthesis gas and a second synthesis gas to a methanol synthesis zone and contacting therein the synthesis gas with a methanol synthesis catalyst to form a methanol synthesis product comprising methanol and unconverted synthesis gas.

2. A process according to claim 1 which further comprises the steps of
   (iv) withdrawing the methanol synthesis product from the methanol synthesis zone and recovering therefrom a methanol-rich liquid stream and a synthesis gas stream; and
   (v) recycling at least a portion of the synthesis gas stream recovered from the methanol synthesis product to the methanol synthesis zone.

3. A process according to claim 1 wherein the first synthesis gas has a stoichiometric number SN and SN=$(H_2—CO_2)/(CO+CO_2)$ of 1.1 or less (including any recycles).

4. A process according to claim 3 wherein the first synthesis gas has a stoichiometric number in the range 0.05 to 1.1.

5. A process according to claim 1 wherein the first synthesis gas comprises synthesis gas recovered from the carbonylation reaction product.

6. A process according to claim 1 wherein the second synthesis gas and the synthesis gas recovered from the carbonylation reaction product has a combined stoichiometric number which is higher than the stoichiometric number of the first synthesis gas.

7. A process according to claim 6 wherein the combined stoichiometric number is in the range 1.5 to 2.5.

8. A process according to claim 1 wherein at least one of the first and second synthesis gas comprises carbon dioxide (including any recycles).

9. A process according to claim 8 wherein carbon dioxide is present in at least one of the first and second synthesis gas in an amount in the range 0.5 to 12 mol %.

10. A process according to claim 1 wherein the aluminosilicate zeolite has a framework structure type selected from MOR, FER, OFF and GME.

11. A process according to claim 10 wherein the zeolite has a framework structure type MOR and is a mordenite.

12. A process according to claim 1 wherein the first synthesis gas and dimethyl ether are reacted in the carbonylation reaction zone under conditions of a temperature in the range 250° C. to 350° C. and a total pressure in the range 50 to 100 barg (5000 kPa to 10,000 kPa).

13. A process according to claim 1 wherein the major portion is 75 to 99 mol % of the synthesis gas recovered from the carbonylation reaction product.

14. A process according to claim 1 wherein the synthesis gas is scrubbed with a scrubbing solvent comprising methanol.

15. A process according to claim 14 wherein the scrubbing solvent further comprises one or more of water and dimethyl ether.

16. A process according to claim 14 wherein the scrubbing solvent is at least a portion of the methanol-rich liquid stream recovered from the methanol synthesis product.

17. A process according to claim 1 wherein carbon dioxide is introduced into the methanol synthesis zone and such carbon dioxide is obtained from one or more of the first synthesis gas and the second synthesis gas.

18. A process according to claim 1 wherein the methanol synthesis catalyst comprises copper.

19. A process according to claim 1 wherein synthesis gas is contacted with the methanol synthesis catalyst under conditions of a temperature of from 210° C. to 270° C. and a total pressure in the range 50 to 100 barg (5000 kPa to 10,000 kPa).

20. A process according to claim 1 wherein methanol is recovered from one or more of the methanol synthesis product withdrawn from the methanol synthesis zone and liquid solvent streams comprising methanol obtained from scrubbing of synthesis gas recovered from the carbonylation reaction product.

21. A process according to claim 2 wherein methanol is recovered from the methanol-rich liquid stream.

22. A process according to claim 2 wherein a portion of the synthesis gas stream recycled to the methanol synthesis zone is vented as a purge stream.

23. A process according to claim 1 wherein methyl acetate is recovered from at least a portion of the methyl acetate-rich liquid stream and the recovered methyl acetate is converted to acetic acid.

24. A process according to claim 1 wherein each of the carbonylation reaction and the methanol synthesis is conducted as a heterogeneous vapour phase reaction.

25. A process according to claim 1 wherein the process is operated as a continuous process.

* * * * *